US008428720B2

(12) United States Patent
Corbucci et al.

(10) Patent No.: US 8,428,720 B2
(45) Date of Patent: Apr. 23, 2013

(54) POSTURE-INDUCED CHANGES TO PHYSIOLOGICAL PARAMETERS

(75) Inventors: Giorgio Corbucci, Cento (IT); Brian B. Lee, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 372 days.

(21) Appl. No.: 12/915,780

(22) Filed: Oct. 29, 2010

(65) Prior Publication Data

US 2012/0108915 A1 May 3, 2012

(51) Int. Cl.
*A61N 1/08* (2006.01)
(52) U.S. Cl.
USPC .............. 607/19; 607/18; 607/63; 600/519; 600/526
(58) Field of Classification Search .................. None
See application file for complete search history.

(56) References Cited

U.S. PATENT DOCUMENTS

| | | | | |
|---|---|---|---|---|
| 3,776,221 | A * | 12/1973 | McIntyre | 600/485 |
| 5,425,750 | A | 6/1995 | Moberg | |
| 6,104,949 | A * | 8/2000 | Pitts Crick et al. | 600/547 |
| 7,313,434 | B2 | 12/2007 | Belalcazar et al. | |
| 7,437,192 | B2 | 10/2008 | Gill et al. | |
| 8,109,879 | B2 * | 2/2012 | Zhang et al. | 600/483 |
| 2005/0216067 | A1 * | 9/2005 | Min et al. | 607/17 |
| 2006/0258952 | A1 | 11/2006 | Stahmann et al. | |
| 2006/0271116 | A1 | 11/2006 | Stahmann et al. | |
| 2006/0293609 | A1 | 12/2006 | Stahmann et al. | |
| 2008/0082001 | A1 | 4/2008 | Hatlestad et al. | |
| 2008/0114407 | A1 | 5/2008 | Pastore et al. | |
| 2008/0243025 | A1 | 10/2008 | Holmstrom et al. | |
| 2008/0262361 | A1 | 10/2008 | Gutfinger et al. | |
| 2008/0300504 | A1 | 12/2008 | Lefkov et al. | |
| 2009/0270748 | A1 * | 10/2009 | Corbucci et al. | 600/509 |
| 2011/0009754 | A1 * | 1/2011 | Wenzel et al. | 600/485 |

FOREIGN PATENT DOCUMENTS

| | | |
|---|---|---|
| EP | 1903937 B1 | 12/2008 |
| WO | WO 2006/126918 A1 | 11/2006 |
| WO | WO 2006/127719 A2 | 11/2006 |
| WO | WO 2006/127719 A3 | 1/2007 |

OTHER PUBLICATIONS

International Search Report for PCT Patent Application No. PCT/US2011/034479, Jul. 19, 2011; 5 pgs.
Bornstein et al., "Cardiac effects of hemodialysis: noninvasive monitoring by systolic time intervals," *Am. J. Med. Sci.*, Mar.-Apr. 1975; 269(2)189-192.
Bornstein et al., "Assessment of the cardiac effects of hemodialysis with systolic time intervals and echocardiography," American Journal of Cardiology, Jan. 15, 1983; 51(2):332-335.
Chan et al., "Detecting change in left ventricular ejection time during head-up tilt-induced progressive central hypovolemia using a finger photoplethysmographic pulse oximetry wave form," *The Journal of Trauma Injury, Infection, and Critical Care*, Feb. 2008; 64(2):390-397.
Chopra et al., "Left ventricular performance in cases with chronic renal failure. A study of systolic time intervals," *Japanese Heart Journal*, Jan. 1987; 28(1):35-40.

(Continued)

*Primary Examiner* — Kennedy Schaetzle
(74) *Attorney, Agent, or Firm* — Carol F. Barry (57) ABSTRACT

Methods and devices for analyzing posture-induced changes to physiological parameters of a patient (e.g., ejection time, heart rate, etc.) to provide an assessment of one or more conditions of the patient.

22 Claims, 6 Drawing Sheets

OTHER PUBLICATIONS

Koji et al., "Left ventricular performance in chronic renal failure before and after hemodialysis assessed by systolic time intervals," *Japanese Circulation Journal*, Apr. 1981; 45:397-402.

Stafford, et al., "Left ventricular systolic time intervals as indices of postural circulatory stress in man." *Circulation*, Mar. 1970; 41:485-492.

Valdivieso et al., "Effect of hemodialysis on myocardial function as assessed by postural stress testing," *Proc. Clin. Dial. Transplant Forum*, 1979; 9:87-92.

Weissler, et al., "Relationships between left ventricular ejection time, stroke volume, and heart rate in normal individuals and patients with cardiovascular disease," *Am. Heart J.*, Sep. 1961; 62(3):367-378.

* cited by examiner

FIG. 6

POSTURE-INDUCED CHANGES TO PHYSIOLOGICAL PARAMETERS

The disclosure herein relates to methods for assessing one or more conditions of a patient using posture-induced changes to one or more heart-related physiological parameters, and further to devices for performing such assessment. For example, the disclosure herein includes methods and devices for monitoring and analyzing posture-induced changes to a patient's ejection time of the left or right ventricle and/or heart rate.

One or more conditions of a patient may be determined by analyzing physiological parameters of a patient such as heart rate, respiration rate, and blood pressure, etc. These physiological parameters may be different for a healthy individual versus one who is unhealthy or suffering from an affliction.

Further, such, physiological parameters may be affected by posture changes. For instance, a patient changing posture from a lying position to a more upright position may affect the patient's venous return due to gravity. As such, the patient's heart rate may increase to compensate for the hemodynamic effect due to gravity.

Hypervolemia, elevated tissue pressure, and increased venomotor tone in heart failure patients often tend to minimize the hemodynamic effects due to gravity. Such conditions may also be present in patients before dialysis. After dialysis, the physiologic effects of gravity on the patient's heart may be restored.

SUMMARY

The disclosure herein relates to methods for assessing one or more conditions of a patient using posture-induced changes to one or more heart-related physiological parameters, and further to devices for performing such assessment. Such methods may include monitoring one or more physiological heart-related parameters, e.g., left and/or right ventricular ejection time, and analyzing the change to the physiological heart-related parameters from before the patient undergoes a posture change (or pre-posture change) to after the posture change (or post-posture change). The posture change may be a change in a patient's posture from a lying position to a position more upright than the lying position.

One exemplary implantable medical device disclosed herein for use in assessment of one or more conditions of a patient may include sensing apparatus to monitor physiological parameters of the patient, a sensing module coupled to the sensing apparatus and configured to receive the monitored physiological parameters, and a control module coupled to the sensing module. The physiological parameters monitored by the sensing apparatus may include the patient's posture and ejection time. The patient's ejection time may include at least one of the patient's left ventricular ejection time and right ventricular ejection time.

The control module may be configured to detect a change in the patient's posture from a lying position to an upright position using the monitored physiological parameters and to determine a posture-induced change to the patient's ejection time using the monitored physiological parameters. The posture-induced change to the patient's ejection time may include a difference between the patient's ejection time before the detected change in the patient's posture and the patient's ejection time after the detected change in the patient's posture. The control module may be further configured to store the posture-induced change to the patient's ejection time and analyze the posture-induced change to the patient's ejection time to provide an assessment of one or more conditions of the patient (e.g., fluid overload).

In one or more embodiments of the exemplary methods and devices disclosed herein, the posture-induced change to the patient's ejection time may be a difference between the patient's average ejection time over a first plurality of heart beats before the detected change in the patient's posture and the patient's average ejection time over a second plurality of heart beats after the detected change in the patient's posture and/or a difference between the patient's average ejection time over a first predetermined period of time before the detected change in the patient's posture and the patient's average ejection time over a second predetermined period of time after the detected change in the patient's posture.

Further, in one or more embodiments of the exemplary devices disclosed herein, the control module may be further configured to analyze the posture-induced change to the patient's ejection time by comparing the posture-induced change to the patient's ejection time to a baseline value and/or by comparing the posture-induced change to the patient's ejection time to a plurality of previous posture-induced changes to the patient's ejection time prior to the posture-induced change to the patient's ejection time to provide one or more trends to be used in the assessment of one or more conditions of the patient.

Yet still further, in one or more embodiments of the exemplary devices disclosed herein, the exemplary devices further include at least one of a therapy delivery module coupled to the control module and a notification module coupled to the control module. The therapy delivery module may be configured to deliver cardiac therapy to the patient and the control module may be further configured to initiate or adjust cardiac therapy using the therapy delivery module based on the assessment of one or more conditions of the patient. The notification module may be configured to alert the patient and the control module may be further configured to initiate an alert using the notification module based on the assessment of one or more conditions of the patient.

One exemplary method disclosed herein for use in assessment of one or more conditions of a patient may include monitoring physiological parameters of the patient. The physiological parameters may include the patient's posture and ejection time (e.g., at least one of the patient's left ventricular ejection time and right ventricular ejection time). The exemplary method may further include detecting a change in the patient's posture from a lying position to an upright position using the monitored physiological parameters and determining a posture-induced change to the patient's ejection time using the monitored physiological parameters. The posture-induced change to the patient's ejection time may be a difference between the patient's ejection time before the detected change in the patient's posture and the patient's ejection time after the detected change in the patient's posture. The exemplary method may further include storing the posture-induced change to the patient's ejection time and analyzing the posture-induced change to the patient's ejection time to provide an assessment of one or more conditions of the patient (e.g., fluid overload).

In one or more embodiments of the exemplary methods described herein, analyzing the posture-induced change to the patient's ejection time may include comparing the posture-induced change to the patient's ejection time to a baseline value and/or comparing the posture-induced change to the patient's ejection time to a plurality of previous posture-induced changes to the patient's ejection time prior to the posture-induced change to the patient's ejection time to provide one or more trends to be used in the assessment of one or more conditions of the patient.

Further, in one or more embodiments of the exemplary methods described herein, the exemplary methods include at least one of initiating or adjusting cardiac therapy to the patient based on the assessment of one or more conditions of the patient and/or alerting the patient based on the assessment of one or more conditions of the patient.

In one or more embodiments of the exemplary methods described herein, analyzing the one or more trends in the plurality of posture-induced changes to the patient's ejection time over time may include determining whether the posture-induced changes to the patient's ejection time have been decreasing over time and providing an assessment that indicates that the patient's heart is progressing towards heart failure if the posture-induced changes to the patient's ejection time have been decreasing over time.

Further, in one or more embodiments of the exemplary methods described herein, the exemplary methods may include determining a posture-induced change to the patient's heart rate using the monitored physiological parameters. The posture-induced change to the patient's heart rate may include a difference between the patient's heart rate before the detected change in the patient's posture and the patient's heart rate after the detected change in the patient's posture. The exemplary methods may further include storing the posture-induced change to the patient's heart rate and analyzing the posture-induced change to the patient's heart rate to verify the assessment of one or more conditions of the patient.

Still further, in one or more embodiments of the exemplary methods described herein, analyzing one or more trends in the plurality of posture-induced changes to the patient's ejection time over time may include analyzing one or more trends in the plurality of posture-induced changes to the patient's ejection time that occur at the same time of the day.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-6. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 1:
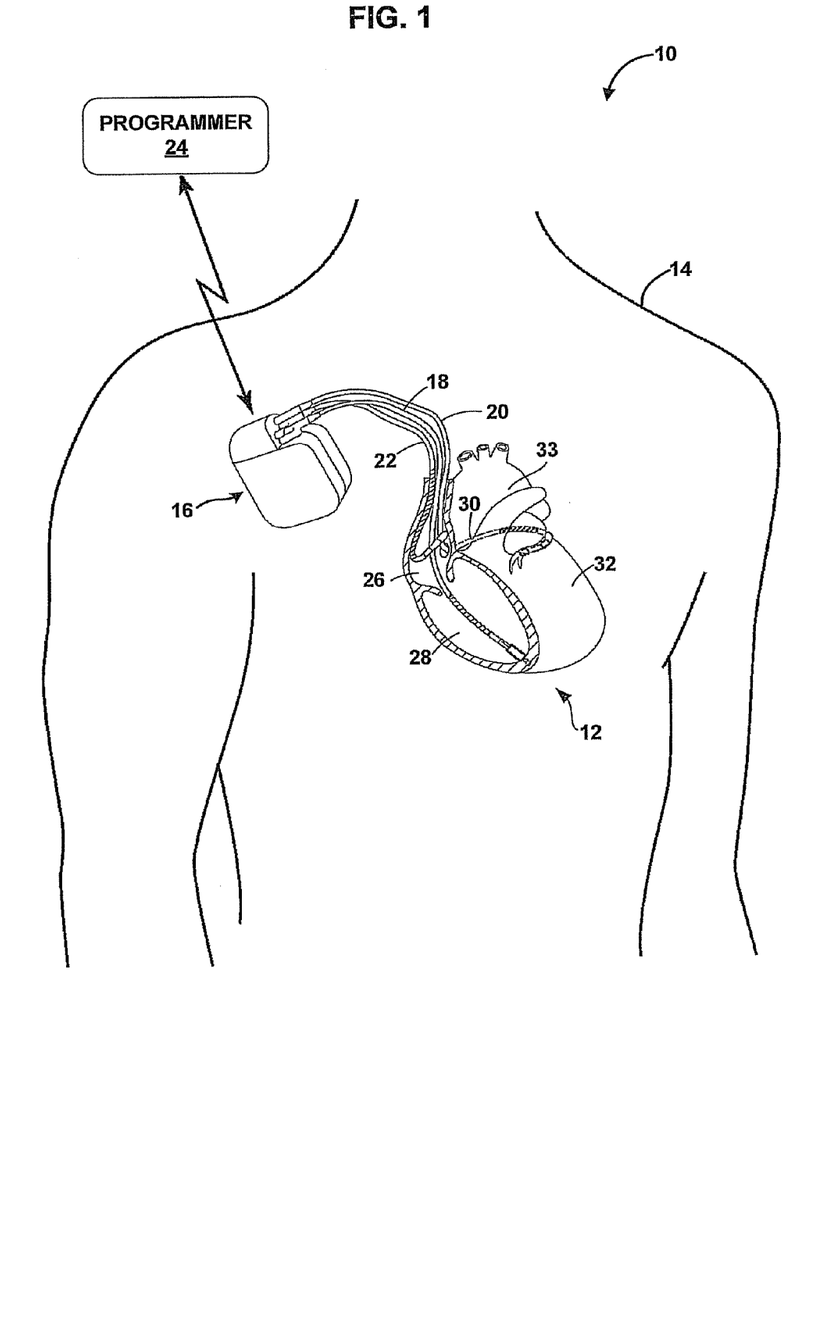
FIG. 1 is a diagram of an exemplary system including an exemplary implantable medical device (IMD).

FIG. 1 is a conceptual diagram illustrating an exemplary therapy system 10 that may be used in assessment of one or more conditions of a patient 14. Patient 12 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes (not shown in FIG. 1) coupled to at least one of the leads 18, 20, 22. In some examples, the IMD 16 provides pacing pulses to the heart 12 based on the electrical signals sensed within the heart 12. The configurations of electrodes used by the IMD 16 for sensing and pacing may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses.

In some examples, the programmer 24 may be a handheld computing device or a computer workstation, which a user, such as a physician, technician, other clinician, and/or patient may use to communicate with the IMD 16. For example, the user may interact with the programmer 24 to retrieve physiological and/or diagnostic information (e.g., posture-induced changes to one or more physiological parameters, assessments of one or more conditions of the patient 14, etc.) from the IMD 16.

The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
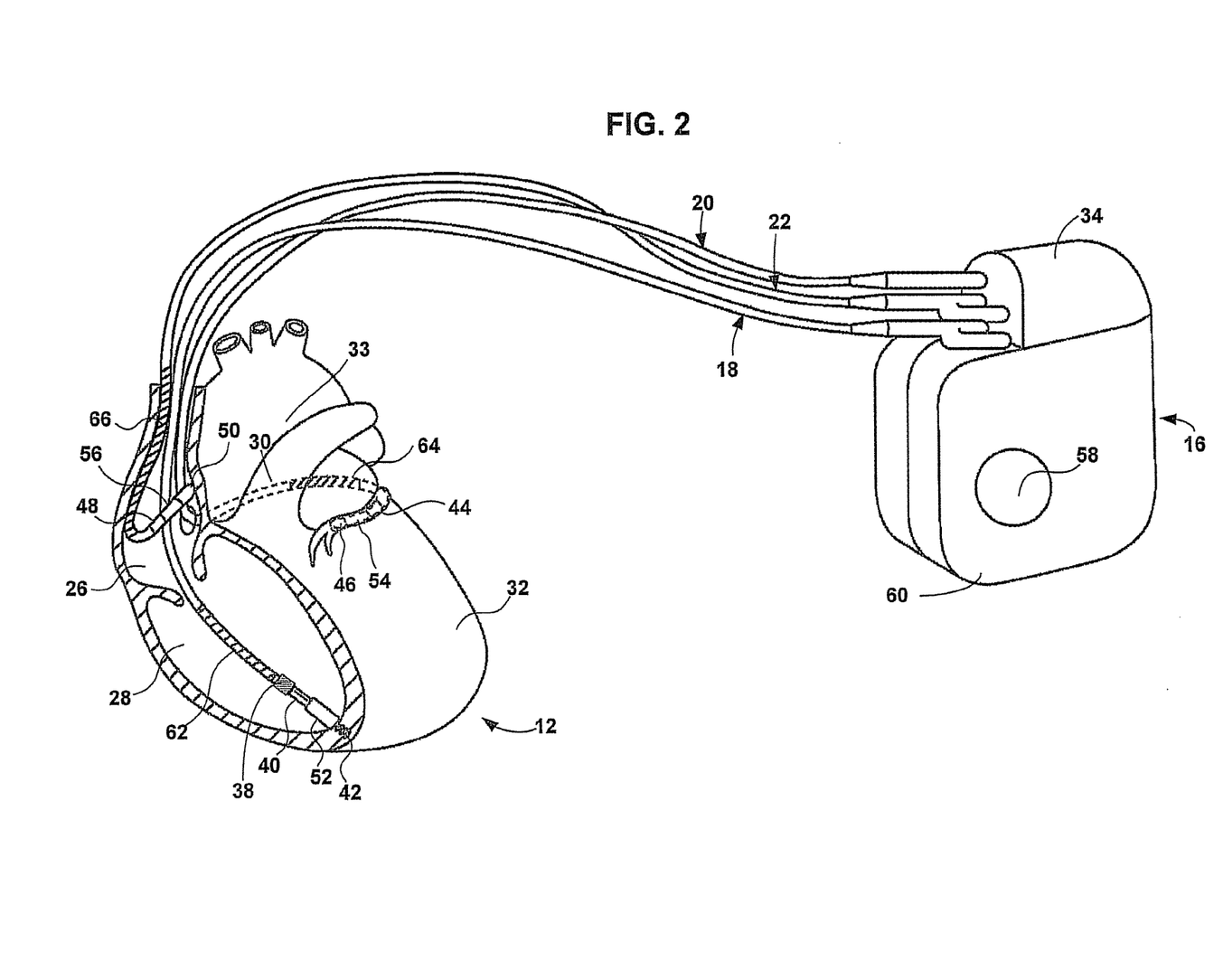
FIG. 2 is a diagram of the exemplary IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module, a sensing module, and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22. As shown in FIG. 2, the pressure sensor 38 is disposed in the right ventricle 28 of the patient's heart 12. The pressure sensor 38 may respond to an absolute pressure inside the right ventricle 28, and may be, e.g., a capacitive and/or piezoelectric pressure sensor. In other examples, the pressure sensor 38 may be positioned within other regions of the heart 12 (e.g., the left ventricle) and may monitor pressure within one or more of the other regions of the heart 12, or may be positioned elsewhere within or proximate to the cardiovascular system of the patient 14 to monitor cardiovascular pressure associated with mechanical contraction of the heart.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the coiled conductors within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66, and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes.

The pressure sensor 38 may be coupled to one or more coiled conductors within the lead 18. In FIG. 2, the pressure sensor 38 is located more distally on the lead 18 than the elongated electrode 62. In other examples, the pressure sensor 38 may be positioned more proximally than the elongated electrode 62, rather than distal to the electrode 62. Further, the pressure sensor 38 may be coupled to another one of the leads 20, 22 in other examples, or to a lead other than the leads 18, 20, 22 carrying stimulation and sense electrodes. In addition, for example, the pressure sensor 38 may be self-contained device that is implanted within the heart 12, such as within the septum separating the right ventricle 28 from the left ventricle 32, or the septum separating the right atrium 26 from the left atrium 33. In such an example, the pressure sensor 38 may wirelessly communicate with a sensing module of the IMD 16.

The configuration of the therapy system 10 illustrated in FIGS. 1-2 is merely one example. In other examples, a therapy system may include epicardial leads and/or patch electrodes instead of or in addition to the transvenous leads 18, 20, 22 illustrated in FIG. 1. Further, in one or more embodiments, the MD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12.

In other examples of therapy systems that provide electrical stimulation therapy to the heart 12, a therapy system may include any suitable number of leads coupled to the IMD 16, and each of the leads may extend to any location within or proximate to the heart 12. For example, other examples of therapy systems may include three transvenous leads located as illustrated in FIGS. 1-2, and an additional lead located within or proximate to the left atrium 33. Still further, other therapy systems may include a single lead that extends from the IMD 16 into the right atrium 26 or the right ventricle 28, or two leads that extend into a respective one of the right ventricle 26 and the right atrium 28.

Figure 3:
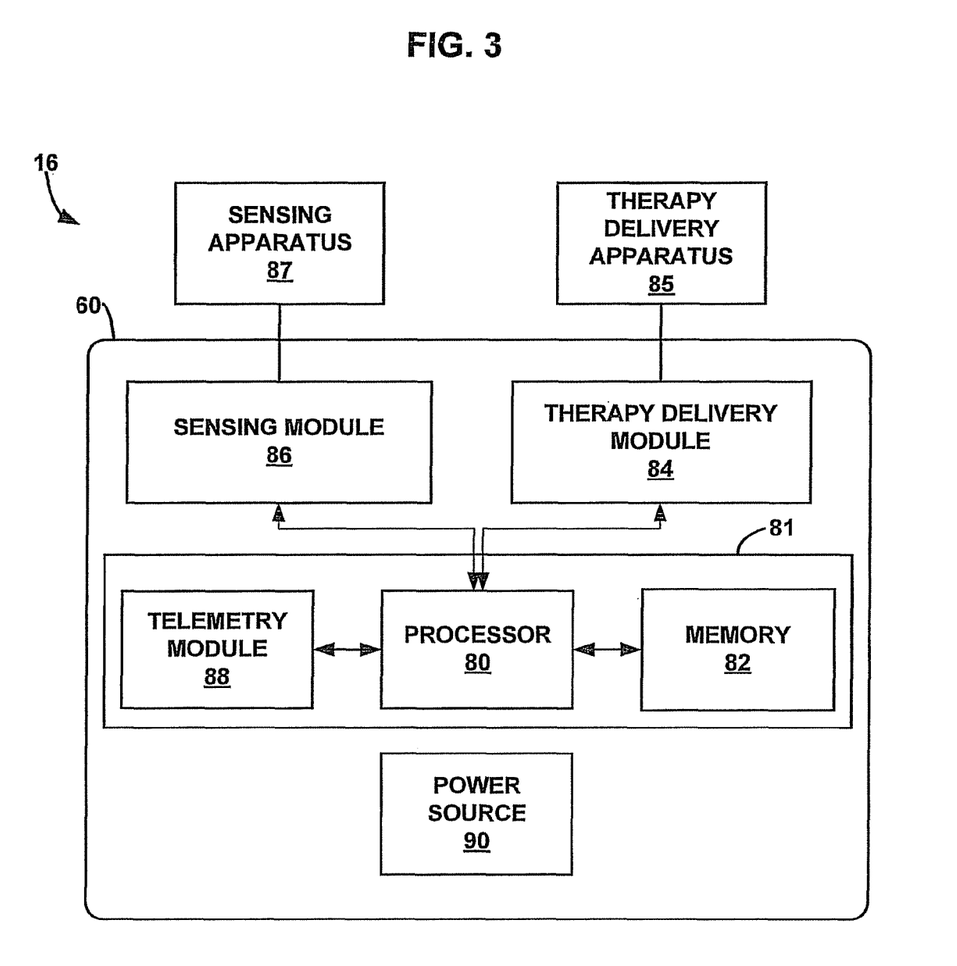
FIG. 3 is a block diagram of an exemplary IMD, e.g., the IMD of FIGS. 1-2.

FIG. 3 is a functional block diagram of one example configuration of IMD 16. As shown, the IMD 16 may include a control module 81, a therapy delivery module 84 (e.g., a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and the control module 81 to perform various functions attributed to the IMD 16 and the control module 81 described herein. Further, the memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The processor 80 of the control module 81 may include any one or more of a microprocessor, a controller, a digital signal processor (DSP), an application specific integrated circuit (ASIC), a field-programmable gate array (FPGA), or equivalent discrete or integrated logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the processor 80 herein may be embodied as software, firmware, hardware, or any combination thereof.

The control module 81 controls the therapy delivery module 84 to deliver therapy (e.g., electrical stimulation therapy) to the heart 12 according to a selected one or more of therapy programs, which may be stored in the memory 82. Specifically, the processor 80 of the control module 81 may control the therapy delivery module 84 to deliver electrical pulses with the amplitudes, pulse widths, frequency, and/or electrode polarities specified by the selected one or more therapy programs.

Although not shown, the IMD 16 may further include a notification module that is configured to provide an alert (e.g., to the patient, a clinician, and/or hospital), such as an audio, somatosensory, visual alert, and/or telemetry to an external data collection server. In some cases, the IMD 16 may send the alert to another device, such as the programmer 24, either automatically or upon request. In at least one embodiment, the control module 81 is configured to initiate an alert using the notification module based on an assessment of one or more conditions of the patient.

The therapy delivery module 84 is coupled (e.g., electrically coupled) to therapy delivery apparatus 85. The therapy deliver apparatus 85 may include, among other therapy delivery devices, the electrodes 40, 42, 44, 46, 48, 50, 58, 62, 64, 66 of the exemplary systems of FIGS. 1-2 (e.g., via conductors of the respective leads 18, 20, 22) and/or the housing electrode 58. The therapy delivery module 84 may be configured to generate and deliver electrical stimulation therapy to the heart 12. For example, the therapy deliver module 84 may deliver defibrillation shocks to the heart 12 via at least two of the plurality of electrodes, e.g., electrodes 58, 62, 64, 66. Further, for example, the therapy delivery module 84 may deliver pacing pulses via the ring electrodes 40, 44, 48 coupled to the leads 18, 20, 22, respectively, and/or the helical electrodes 42, 46, 50 of the leads 18, 20, 22, respectively. In some examples, the therapy delivery module 84 delivers pacing, cardioversion, and/or defibrillation stimulation in the form of electrical pulses.

The sensing module 86 is coupled (e.g., electrically coupled) to sensing apparatus 87, e.g., to monitors signals from the sensing apparatus 87. The sensing apparatus 87 may include the electrodes 40, 42, 44, 46, 48, 50, 58, 62, 64, 66 to monitor electrical activity of the heart 12, e.g., impedance signals between two or more electrodes (e.g., right and/or left ventricle impedance, subcutaneous impedance, impedance waveform during ejection, impedance waveform during filling, etc.), electrocardiogram (ECG) signals, etc. The impedance signals may be used to monitor stroke volume (SV), ejection time (ET), etc. The ECG signals may be used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc. The sensing apparatus 87 may further include one or more pressure sensors, posture sensors (e.g., 2-D and/or 3-D accelerometers), heart sound sensors, activity sensors, perfusion sensors, etc. to monitor one or more heart-related physiological parameters such as, e.g., patient posture, ejection time, stroke volume, cardiac output, pre-ejection time, filling time, normalized ejection time % (ejection time divided by the R-R interval expressed as a percentage), etc.

The one or more posture sensors of the sensing apparatus 87 may provide signals or values corresponding to the posture of the patient 14, the activity level of the patient 14, etc. Using such signals or values, the IMD 16 (e.g., the control module 81) may determine whether the patient 14 has made a change in posture. For example, the IMD 16 may use one or more accelerometers to detect changes in the patient's posture from a lying position to an upright position or from an upright position to a lying position. As used herein, a lying position may be any position in which the patient's torso is less than completely vertical (e.g., perpendicular to a flat ground surface). In other words, a patient's torso may be less than completely vertical when it forms less than a 90 degree angle with the ground surface. The lying position may be include supine, prone, right lateral decubitus (e.g., the patient lying on their right side), and left lateral decubitus (e.g., the patient lying on their left side) positions. Further, the patient may be in a lying position while resting in a reclined chair (e.g., having their torso forming less than a 90 degree angle with the ground surface).

Further, as used herein, an upright position may be simply a more upright position than the patient's lying position. For example, if the patient's lying position is resting in a recliner with their torso at a 45 degree angle (e.g., to the ground surface), an upright position may be sitting with their torso at a 70 degree angle. Further, for example, the upright position may simply be a standing posture (e.g., the patient standing on their two feet on a ground surface or floor such that they are substantially vertical).

One example of a posture sensor capable of detecting patient posture, motion, and activity is an accelerometer, such as a multi-axis accelerometer. A three-axis accelerometer, e.g., may be able to detect motion and posture by detecting acceleration along three axes. An exemplary accelerometer that may be used with the methods and devices disclosure herein may be described in U.S. Pat. No. 5,425,750 to Moberg, which is incorporated by reference in its entirety.

The sensing apparatus 87 is further capable to measure and/or monitor the ejection time of the right and/or left ventricle. For example, the sensing apparatus 87 may utilize two or more electrodes and/or one or more pressure sensors (e.g., pressure sensors 38) located within the right and/or left ventricle to measure and/or monitor the ejection time of the right and/or left ventricle. Further, the control module 81 may use the data collected using the sensing apparatus 87 to calculate the ejection time of the right and/or left ventricle.

With respect to the electrodes, the sensing module 86 may also include a switch module to select which of the available electrodes are used to sense heart activity. In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier. In response to the signals from the control module 81, the switch module of the sensing module 86 may couple the outputs from the selected electrodes to one or more of the sensing channels.

The telemetry module 88 of the control module 81 may include any suitable hardware, firmware, software, or any combination thereof for communicating with another device, such as the programmer 24 (FIG. 1). For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Further, although the IMD 16 as described herein may include a therapy delivery module coupled 84 and therapy delivery apparatus 85, and may be used to deliver therapy (e.g., in view of an assessment of one or more conditions) using such items, in one or more embodiments, the IMD 16 and/or any other device may utilize the methods and/or techniques described herein without delivering therapy. For example, an exemplary device may not include a therapy deliver module 84 and/or therapy delivery apparatus 85 and, as such, may not deliver therapy, but such exemplary device may still be configured to assess one or more conditions of a patient using posture-induced changes to one or more heart-related physiological parameters.

As described herein, a patient changing posture from a lying position to a more upright position may affect the patient's venous return due to gravity, and as a result, the patient's stroke volume and/or ejection time may decrease and heart rate may increase to compensate for the hemodynamic effect due to gravity. One or more conditions (e.g., congestive heart failure, fluid overload, etc.) may inhibit the hemodynamic effects of one or more physiological parameters due to gravity.

Stroke volume may be estimated through the measurement of ejection time. For instance, stroke volume and ejection time may be substantially linearly related (e.g., as stroke volume increases, ejection time increases and vice versa). As described herein, ejection time may be measured using right ventricular pressure, right ventricular impedance, heart sounds, subcutaneous impedance, subcutaneous perfusion, etc. For example, an impedance waveform may be monitored using an RV lead immediately after RV pacing or a sensed RV activity (e.g., R-wave, contraction, etc.) for at least 300 milliseconds (ms). The start of ejection time can be determined through the morphologic analysis of the impedance waveform within a first time window of 150 ms starting from RV pacing or a sensed RV activity. The end of ejection time can be determined through the morphologic analysis of the impedance waveform within a second time window of 150 ms centered on T-wave sensing. Further, for example, the impedance waveform may simply be monitored in a time window of about 350 ms from RV pacing or a sensed RV activity to determine ejection time. Still further, for example, detection of the first heart sound (FHS), an indicator of the onset of the ejection, and the second heart sound (SHS), an indicator of the offset of ejection, may be used to determine ejection time. Although described separately, each of these exemplary techniques may be used alone or in combination for a more precise estimation of ejection time. Further, right ventricular ejection time and left ventricular ejection time may have parallel trends, and as such, either or both of them may be used to estimate stroke volume.

Figure 4:
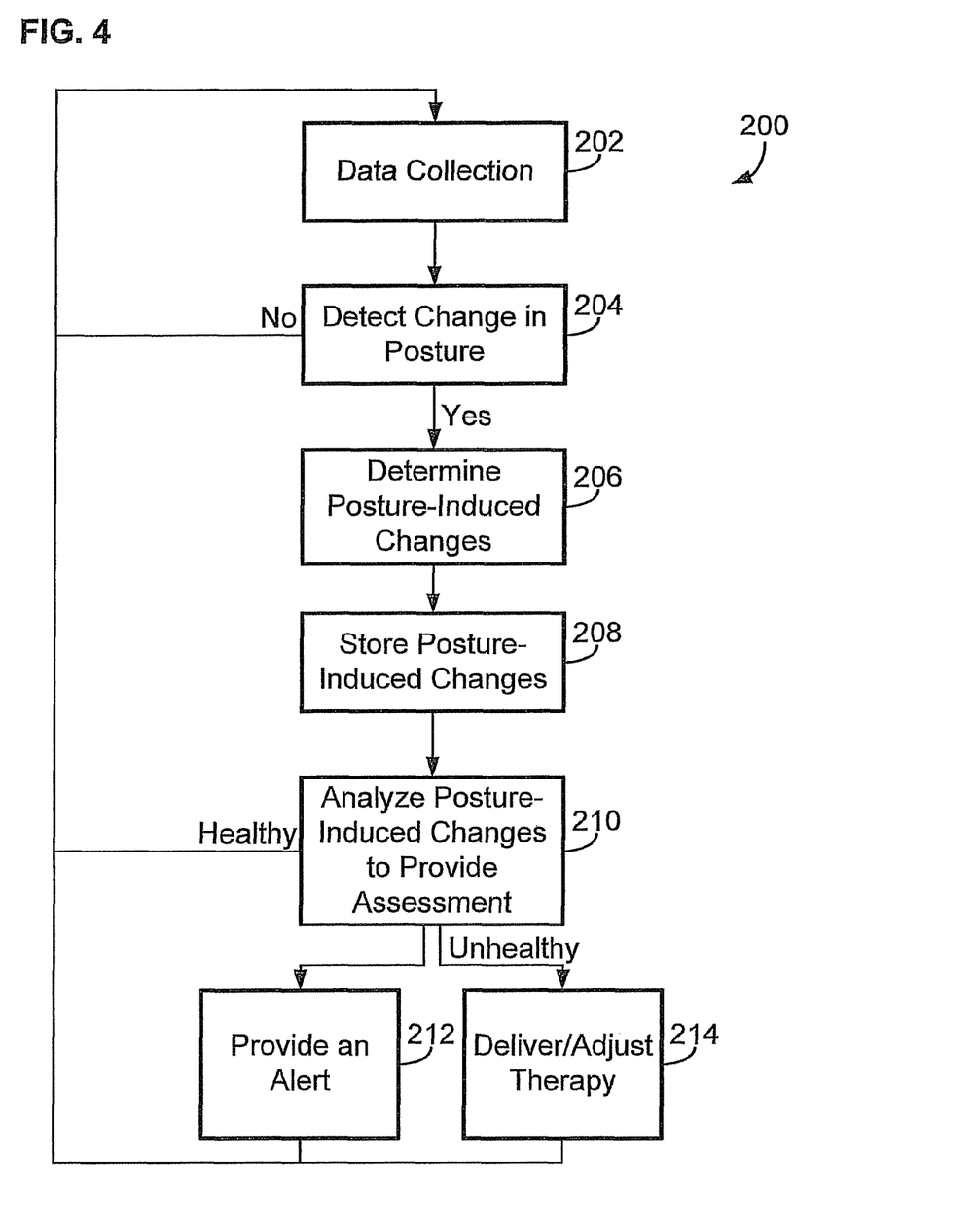
FIG. 4 is a flow chart of an exemplary method for use in assessment of one or more conditions of a patient, e.g., using the IMDs of FIGS. 1-3.

A generalized method 200 for use in assessment of one or more conditions of a patient's heart is diagrammatically depicted in FIG. 4. Method 200 is intended to illustrate the general functional operation of the devices and/or systems described herein, and should not be construed as reflective of a specific form of software or hardware necessary to practice all of the methods described herein. It is believed that the particular form of software will be determined primarily by the particular system architecture employed in the device (e.g., IMD 16) and by the particular detection and therapy delivery methodologies employed by the device and/or system. Providing software and/or hardware to accomplish the described methods in the context of any modern IMD, given the disclosure herein, is within the abilities of one of skill in the art.

The method 200 of FIG. 4 includes data collection 202. Data collection 202 may include monitoring one or more physiological parameters of a patient (e.g., at least one physiological parameter) such as, for example, the patient's posture, the electrical activity of the patient's heart, the ejection time of the patients' left and/or right ventricle, etc.

The data collected 202 may be analyzed to detect and/or determine a change in the patient's posture 204. For example, the monitored physiological parameters with respect to a patient's posture may indicate that the patient has moved from a lying position to an upright position, from an upright position to a lying position, from a lying position to a more upright position, from an upright position to a less upright position, from a sitting position to a standing position, from a standing position to a sitting position, from a reclined sitting/laying position to a less reclined sitting/laying position, from a reclined sitting/laying position to a more reclined sitting/laying position, etc.

Although an arrow is shown in FIG. 4 extending from data collection 202 to posture change detection/determination 204, the data collection 202 and the posture change detection/determination 204, as well as other processes described herein, may be executed concurrently as opposed to sequentially or periodically.

If a posture change is detected 204 (e.g., if the physiological parameters of the patient indicate that the patient's posture has changed), the method 200 proceeds to determine the posture-induced changes to one or more physiological parameters of the patient 206, e.g., changes to the patient's ejection time, changes to the patient's heart rate, etc., due, in part, to the posture change. In at least one embodiment, the change to the patient's ejection time may be the difference or variation between the patient's ejection time before the change in the patient's posture and the patient's ejection time after the change in the patient's posture. In at least another embodiment, the change to the patient's heart rate may be the difference or variation between the patient's heart rate before the change in the patient's posture and the patient's heart rate after the change in the patient's posture. In other words, a posture-induced change to a physiological parameter may simply be the difference or variation between a physiological parameter pre-posture change to post-posture change. Such posture-induced change to a physiological parameter may be represented as a percentage of change from the value of the physiological parameter prior to the posture change.

Figure 5A:
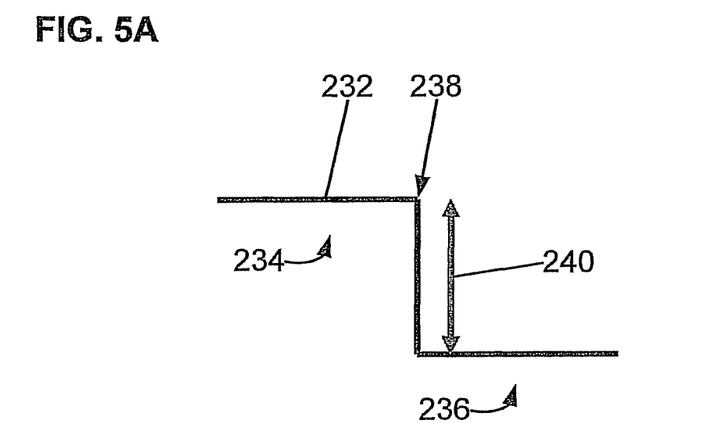
FIGS. 5A-5B are exemplary graphical depictions of posture-induced changes to a physiological parameter.
Figure 5B:
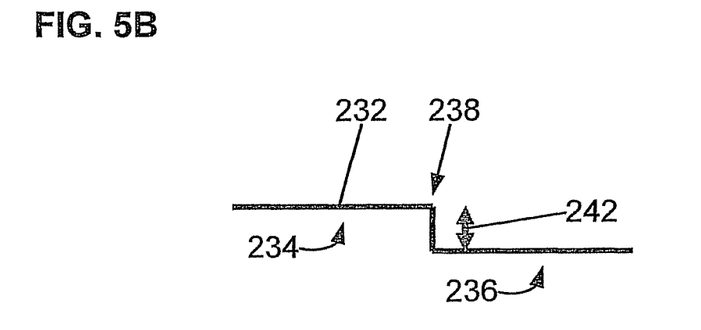

For example, as shown in FIGS. 5A-5B, a physiological parameter 232 of a patient is plotted over a time period within which a posture change 238 occurs. The physiological parameter 232 depicted in FIG. 5A is of a healthy patient while the physiological parameter 232 depicted in FIG. 5B is of an unhealthy patient (e.g., a patient progressing towards heart failure, a patient that is undergoing fluid overload, etc.).

During the time period 234 prior to the posture change 238, the physiological parameter 232 may be at a first value or level. During the time period 236 after the posture change 238, the physiological parameter 232 may be at a different or second value or level. In one embodiment, the posture-induced physiological parameter may be the difference 240, 242 between the first value/level and the second value/level. In other words, the difference may be the absolute value of the subtraction of the first value of the physiological parameter 232 (i.e., from the time period 234 prior to the posture change 238) from the second value of the physiological parameter 232 (i.e., from the time period 236 after to the posture change 238).

Although, as depicted, the physiological parameter 232 (e.g., ejection time, stroke volume, etc.) decreases after the posture change 238, the physiological parameter 232 may actually increase, e.g., depending on the physiological parameter 232 being monitored. For example, a posture change from a lying position to an upright position should induce an increase in a patient's heart rate. Also, the opposite behavior may be observed during the opposite posture change, e.g., from an upright position to a lying position. For example, a posture change from an upright position to a lying position should induce an increase in the ejection time/stroke volume of a patient's heart and a decrease in the patient's heart rate.

The posture-induced changes to ejection time, heart rate, and/or any other of the one or more physiological parameters may be sampled for a period before and after the posture change. For example, the posture-induced change may be a difference between the average of the physiological parameter over a first selected plurality of heart beats (e.g., more or less than 4 beats, more or less than 8 beats, more or less than 16 beats, more or less than 32 beats, and/or more or less than 64 beats) before the detected change in the patient's posture and the average of the physiological parameter over a second selected plurality of heart beats (e.g., more or less than 4 beats, more or less than 8 beats, more or less than 16 beats, more or less than 32 beats, and/or more or less than 64 beats) after the detected change in the patient's posture. In at least one embodiment, the posture-induced change to one or more physiological parameters of a patient may be a difference between the patient's average ejection time over a first plurality of heart beats (e.g., about 4 beats to about 64 beats) before the detected change in the patient's posture and the patient's average ejection time over a second plurality of heart beats (e.g., about 4 beats to about 64 beats) after the detected change in the patient's posture.

Further, for example, the posture-induced change may be a difference between the average of the physiological parameter over a first predetermined period of time (e.g., more or less than 60 seconds, more or less than 30 seconds, more or less than 20 seconds, more or less than 10 seconds, and/or more or less than 5 seconds) before the detected change in the patient's posture and the average of the physiological parameter over a second predetermined period of time (e.g., more or less than 60 seconds, more or less than 30 seconds, more or less than 20 seconds, more or less than 10 seconds, and/or more or less than 5 seconds) after the detected change in the patient's posture. In at least one embodiment, the posture-induced change to one or more physiological parameters of a patient may be a difference between the patient's average ejection time over a first predetermined period of time (e.g., about 5 seconds to about 60 seconds) before the detected change in the patient's posture and the patient's average ejection time over a second predetermined period of time (e.g., about 5 seconds to about 60 seconds) after the detected change in the patient's posture.

As described herein, one of the physiological parameters that may be monitored for a posture-induced change is the left and/or right ventricular ejection time. The posture-induced changes to left and/or right ventricular ejection time may be indicative (e.g., a marker) of fluid overload because, e.g., variations in ejection time during postural changes may decrease as fluid overload increases and may be restored to a normal value when fluid balance has been restored.

After determining the posture-induced change 206, the method 200 proceeds to store the posture-induced change 208 (e.g., in the memory 81 of the IMD 16) and analyze the posture-induced change to provide an assessment of one or more conditions of a patient heart 210.

As shown, e.g., in FIGS. 5A-5B, the difference 240 (e.g., the magnitude or absolute value) of the physiological parameter 232 of the healthy patient is greater than the difference 242 of the unhealthy patient. As such, the magnitude or absolute value of the difference between a physiological parameter monitored before a posture change and after a posture change may be indicative of one or more conditions of a patient (e.g., fluid overload, heart failure). In other words, the magnitude or absolute value of the difference of a physiological parameter pre-posture change to post-posture change may be indicative of one or more conditions of a patient. Such difference may be referred to as a posture-induced change to a physiological parameter. The posture-induced change may then be compared, e.g., to a min/max limit, baseline values, historical values, pre-set values, etc., to determine whether the posture-induced change may indicate one or more conditions of a patient. In at least one embodiment, the posture-induced change may be calculated, stored, and/or used as a percentage difference, e.g., the absolute value of the pre-posture change value subtracted from the post-posture change value, then divided by the pre-posture change value, and provided as a percentage.

For example, the ejection time of the left and/or right ventricle of a patient may be monitored and posture-induced changes to the patient's ejection time may be determined and compared to a baseline value (e.g., selected by a clinician, automatically calculated by an IMD itself, etc). The baseline value may be the an acceptable percentage difference between an acceptable value representative of the physiological parameter prior to the posture change, and an acceptable value representative of the physiological parameter after the posture change. In other words, the baseline value may be the percentage change in the physiological parameter from pre-posture change to post-posture change that may be indicative of a healthy patient.

In at least one embodiment, if a posture-induced change to ejection time or heart rate, calculated as a percentage difference relative to a pre-posture change level, is greater than about a 20 percent change (or, e.g., greater than about a 5 percent change, greater than about a 10 percent change, greater than about a 15 percent change, or greater than about a 25 percent change), it may indicate that the patient is healthy. In other words, for example, in a normal healthy patient, without fluid overload, the amount of change in ejection time or heart rate due to the posture change should not be decreased (e.g., it is still greater than a 20 percent change just as it should be in a healthy patient). Likewise, if a posture-induced change to ejection time or heart rate, also calculated as a percentage difference relative to a pre-posture change level, is less than about a 20 percent change (or, e.g., less than about a 5 percent change, less than about a 10 percent change, less than about a 15 percent change, or less than about a 25 percent change), it may indicate that the patient is unhealthy (e.g., the patient is at risk for heart failure, the patient may be undergoing fluid overload to at least some degree, etc.). In other words, the fluid overload decreases the amount of change (e.g., an unhealthy patient may have a less than about a 10 percent change due to the particular posture change) when that particular change in posture should be causing a larger change in the physiological parameter (e.g., the person when healthy would have a change greater than 20 percent). As such, an indication of fluid overload is indicated.

As such, the analysis 210 may include comparing the determined posture-induced changes to one or more of the physiological parameters of the patient to a selected value (e.g., a baseline percentage of change, such as when the person is healthy). In at least one embodiment, the selected value may be established as being indicative of healthy heart function in response to posture changes (and, in turn, gravity effects). For example, as described herein, a posture-induced change to the patient's ejection time (e.g., the absolute vale of the pre-posture change value subtracted from the post-posture change value, divided by the pre-posture change value, and provided in percentage form) less than a 10 percent change may indicate heart failure and/or is in a fluid overload condition. As such, if the posture-induced change to a patient's ejection time is less than 10 percent, then the analysis may provide an assessment that indicates that the patient is at risk of heart failure and/or fluid overload.

Further, the analysis 210 may include comparing a present posture-induced change of one or more physiological parameters of the patient (e.g., a currently detected change, such as the most recently detected change) to a plurality of previous posture-induced changes of the one or more physiological parameters of the patient detected prior to the present posture-induced change. For example, a plurality of posture-induced changes may have been stored 208 over a selected time period, and an average of the plurality of posture-induced changes may establish an acceptable baseline value to compare with the present posture-induced change. However, the present posture-induced change to the physiological parameter detected by the system may be compared to any suitable limit (e.g., max/min), and such comparison is not limited to only a baseline determined based on prior detected measurements. For example, such limits may be limits based on test data from a plurality of patients or limits based on test data from the same patient.

Although analyzing a single posture-induced change may provide an assessment of one or more conditions of a patient (e.g., by comparison to a baseline or other threshold limit), the trend of posture-induced changes to one or more physiological parameters of a patient over time may also provide further assessment of one or more conditions of the patient. For example, the analysis 210 may include analyzing a trend in a plurality of posture-induced changes to one or more physiological parameters of a patient (e.g., right and/or left ejection time, heart rate, etc.) over time, or, in other words, determining a trend in the data through such analysis.

Figure 6:
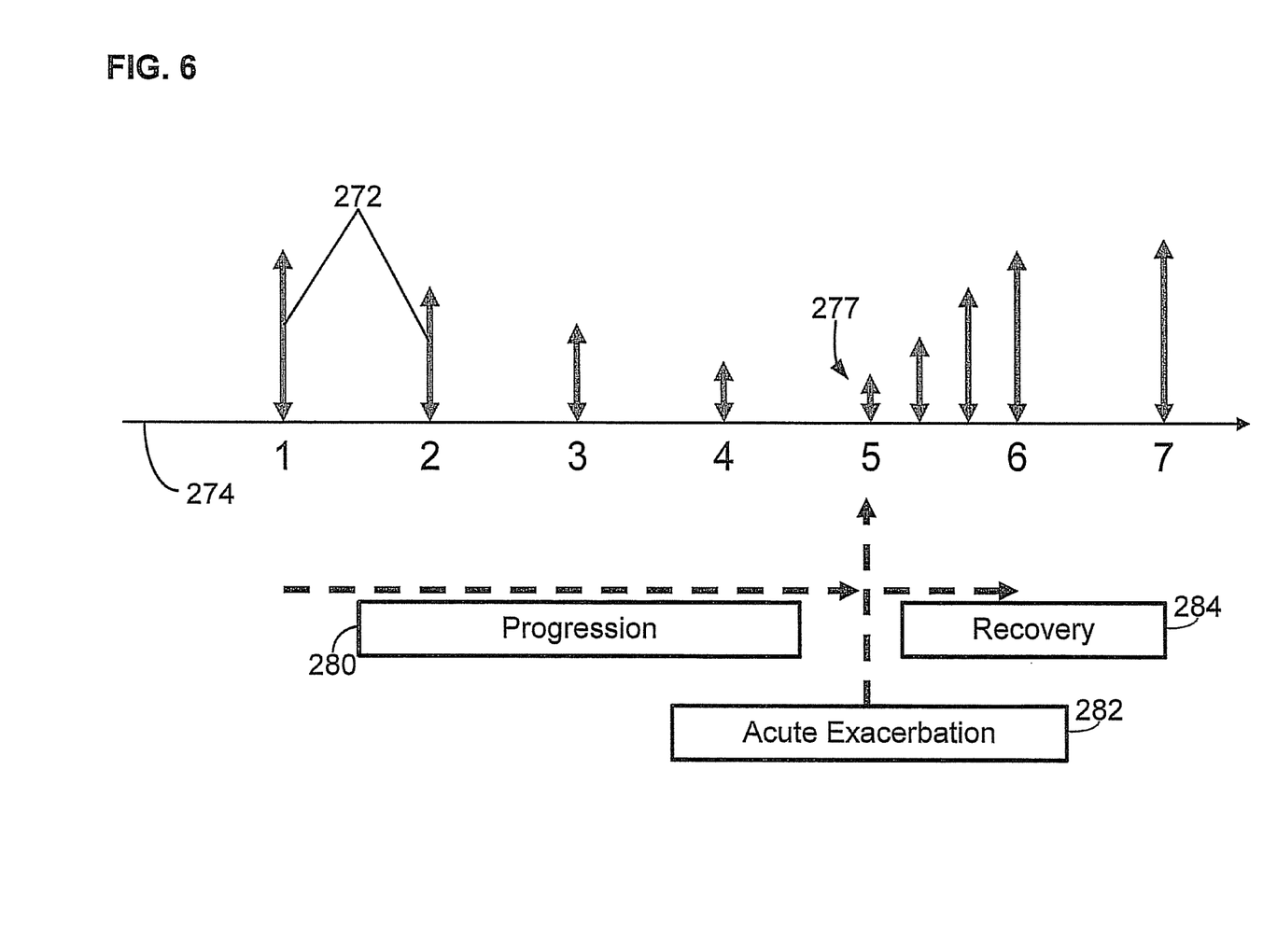
FIG. 6 is an exemplary graphical depiction of posture-induced changes to a physiological parameter over a time period.

A plurality of posture-induced changes to ejection time 272 of a patient over time are depicted in FIG. 6. The x-axis 274 represents time in days. As shown, the posture-induced changes to ejection time 272 decrease, or trend downwardly, after day 1 until day 5, at which time an acute exacerbation of heart failure 282 occurs. Afterwards, the posture-induced changes to ejection time 272 increase or trend upwardly. In other words, prior to the acute exacerbation of heart failure 282, the patient may have progressed 280 towards fluid overload and/or heart failure, e.g., as correlated with the downward trend of the posture-induced changes to ejection time 272. In other words, for example, due to fluid overload, the change in ejection time caused by a particular type of posture change (e.g., transitioning from a lying state to a more upright position) decreased each day for several days. After the acute exacerbation 282, the patient progressed towards recovery, e.g., as correlated with the upward trend of the posture-induced changes to ejection time 272.

As such, one or more trends of posture-induced changes to one or more physiological parameters of a patient (e.g., a pattern in a plurality of posture-induced changes over time, such as changes occurring for the same posture change such as from the same lying position to the same upright position) may be useful to analyze to provide an assessment of one or more conditions of a patient. In at least one embodiment, the analysis 210 may include determining whether the posture-induced changes to one or more of the physiological parameters of the patient (e.g., ejection time) have been increasing, decreasing, or constant over time. For example, if the trend of posture-induced changes to the patient's ejection time and/or heart rate has been decreasing, the assessment provided by the analysis may indicate a progression towards fluid overload and/or heart failure. Further, for example, if the trend of posture-induced changes to the patient's ejection time and/or heart rate has been constant, the assessment provided by the analysis may indicate that the patient is healthy.

A trend that indicates that one or more conditions of a patient are worsening may trigger or initiate additional monitoring of the patient. In at least one embodiment, the methods and/or devices described herein may include an extra verification or validation process to confirm the findings indicated by a trend that indicates that one or more conditions of the patient are worsening. For example, if the posture-induced changes to one or more physiological parameters indicate that one or more conditions of the patient are worsening (e.g., the trend in posture-induced changes to the patient's ejection time shows a decrease), then analysis of posture-induced changes to one or more physiological parameters (e.g., the patient's heart rate) may be used to verify the assessment of one or more conditions of the patient. In at least one embodiment, the posture-induced changes to the patient's heart rate may be compared to a baseline value to confirm, validate, or verify a finding (e.g., based on ejection time changes) that one or more conditions of the patient are worsening.

In at least another embodiment, if the posture-induced changes to one or more physiological parameters indicate that one or more conditions of the patient are worsening (e.g., the trend in posture-induced changes to the patient's ejection shows a decrease), then the methods and/or devices described herein may increase the monitoring of one or more parameters associated with one or more conditions of the patient. For example, the frequency at which various parameters may be monitored may be increased beyond normal operating parameters (e.g., instead of monitoring various physiological parameters once a day, the devices and/or methods may monitor various physiological parameters multiple times a day). Further, for example, additional monitoring may be triggered or initiated that may not normally occur.

Further, the posture-induced changes to one or more physiological parameters of a patient may fluctuate depending on multiple factors such as, e.g., the specific type of posture change, the time of day, the excitement and/or activity level of the patient, etc. As such, an analysis of a single posture-induced change or a trend of posture-induced changes to one or more physiological parameters of a patient may take into consideration such factors, such as the specific type of posture change. For example, a posture-induced change to a physiological parameter, e.g., ejection time, in response to a patient moving from a horizontal, lying position to a vertical, standing upright position may be different than a posture-induced change in response to the same patient moving from a sitting position to a vertical, standing upright position.

Further, for example, a posture-induced change to a physiological parameter, e.g., ejection time, that occurs immediately after a patient wakes up (e.g., getting out of bed) when the patient's activity level is low may be different than a posture-induced change that occurs later in the day after the patient's activity level may have been elevated.

As such, the methods described herein may take into consideration one or more of the factors that may affect the posture-induced changes to one or more physiological parameters (e.g., such as the particular type of posture change, the time of day, etc.) such that the analysis of posture-induced changes may be more predictable and/or consistent. More specifically, the methods may only record/store, analyze, and/or compare posture-induced changes (e.g., compared to base line values, within a trend, compared to each other, etc.) that occur in the same or similar circumstances and/or factors.

For example, in at least one embodiment, the posture-induced changes to one or more physiological parameters of a patient that are to be used in analysis may be only collected at the same time of the day, e.g., once a day in the morning after the patient wakes up and makes their first posture change from a lying position to a more upright position. Further, for example, the posture-induced changes to one or more physiological parameters of a patient may be collected in the afternoon (after rest) or at night when a patient makes a posture change from an upright position to lying position. Although described separately, in at least one embodiment, the posture-induced changes collected in the morning, evening, or afternoon may be analyzed in conjunction with one another (e.g., the absolute values of posture-induced changes may be similar).

As described, one of the factors that may affect the posture-induced changes to one or more physiological parameters is the specific type of posture change. As a result, the methods and devices described herein may only store/record, analyze, and/or compare postured-induced changes to physiological parameters that correspond to the same specific type of posture change. For example, only posture-induced changes to one or more physiological parameters induced by posture changes from a horizontal, lying position to a vertical, upright position may be monitored and analyzed.

Further, physiological parameter data may be collected for a plurality of postures, e.g., lying positions and upright positions, and such data may be compared to each other to establish baseline values (of one or more physiological parameters) for a plurality of posture changes. In other words, the methods described herein may determine what lying and upright positions are common enough to provide reliable trends. For example, posture-induced changes to one or more physiological parameters of a patient may be monitored for a selected period of time (e.g., over the course of a week) and baselines values (of a posture-induced changes) may be established for each, specific common lying position and each, specific upright position. In effect, baseline values may be established for a plurality of posture changes, each posture change being a different combination of common lying positions and common upright positions (e.g., by subtracting the baseline values for each specific common lying position and each specific upright position). As a result, each of the plurality of posture changes may have specific baseline values for use in analysis.

As depicted in FIG. 4, the method 200 may return to data collection 202 or proceed to provide an alert 212 and/or deliver/adjust therapy 214. If it is determined that the posture-induced changes may indicate that the patient is not healthy, the method 200 may return to data collection 202. If it is determined that the posture-induced changes indicate that the patient is unhealthy, then the method 200 may provide an alert 212 and/or deliver/adjust therapy 214. After the alert has been provided 212, and/or cardiac therapy has been delivered/adjusted 214, the method 200 may return to data collection 202.

Providing an alert 212 may include delivering an alert to the patient or a caregiver. The alert may include one or more of an audible signal, a text message, and/or some other signal to draw attention to the patient's worsening condition. For example, the alert may be wirelessly transmitted to the programmer 24. Further, in one or more embodiments, the alert may be transmitted to an external device that is connected to the Internet such that the alert may also be transmitted to a clinician overseeing the patient.

The method 200 may utilize one or more therapies (e.g., cardiac therapy, fluid removal therapies, medication, drug delivery therapy, etc.) to the patient described herein. Depending on the assessment of the one or more conditions of the patient, such therapies may be delivered and/or adjusted 214 to treat the one or more conditions. For example, if the assessment 210 indicates that the patient is likely undergoing fluid overload that may lead to heart failure, the method 200 may deliver pacing therapy to the patient's heart, therapy to remove fluid, etc. Further, for example, if the assessment 210 indicates that the patient is likely undergoing fluid overload that may lead to heart failure and the patient's heart rate is less than 70 beats per minute, the rate at which the patient's heart is being paced may be increased to 80 beats per minute to increase the cardiac output to, e.g., facilitate fluid removal.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An implantable medical device for use in assessment of one or more conditions of a patient comprising:
sensing apparatus to monitor physiological parameters of the patient, wherein the physiological parameters comprise the patient's posture and ejection time, wherein the patient's ejection time comprises at least one of the patient's left ventricular ejection time and right ventricular ejection time;
a sensing module coupled to the sensing apparatus and configured to receive the monitored physiological parameters; and
a control module coupled to the sensing module and configured to:
detect a change in the patient's posture between a lying position and an upright position using the monitored physiological parameters,
determine a posture-induced change to the patient's ejection time using the monitored physiological parameters, wherein the posture-induced change to the patient's ejection time comprises a difference between the patient's ejection time before the detected change in the patient's posture and the patient's ejection time after the detected change in the patient's posture,
store the posture-induced change to the patient's ejection time, and
analyze the posture-induced change to the patient's ejection time to provide an assessment of one or more conditions of the patient, wherein the one or more conditions of the patient comprise fluid overload.

2. The device of claim 1, wherein the posture-induced change to the patient's ejection time further comprises a difference between the patient's average ejection time over a first plurality of heart beats before the detected change in the patient's posture and the patient's average ejection time over a second plurality of heart beats after the detected change in the patient's posture.

3. The device of claim 1, wherein the posture-induced change to the patient's ejection time further comprises a difference between the patient's average ejection time over a first predetermined period of time before the detected change in the patient's posture and the patient's average ejection time over a second predetermined period of time after the detected change in the patient's posture.

4. The device of claim 1, wherein the control module is configured to analyze the posture-induced change to the patient's ejection time by comparing the posture-induced change to the patient's ejection time to a baseline value.

5. The device of claim 1, wherein the control module is configured to analyze the posture-induced change to the patient's ejection time by comparing the posture-induced change to the patient's ejection time to a plurality of previous posture-induced changes to the patient's ejection time prior to the posture-induced change to the patient's ejection time to provide one or more trends to be used in the assessment of one or more conditions of the patient.

6. The device of claim 1, wherein the analysis of the posture-induced change to the patient's ejection time provides an assessment that indicates that the patient is afflicted with fluid overload if the posture-induced change to the patient's ejection time is less than a 10 percent change.

7. The device of claim 1 further comprising at least one of:
a therapy delivery module coupled to the control module and configured to deliver cardiac therapy to the patient, wherein the control module is further configured to initiate or adjust cardiac therapy using the therapy delivery module based on the assessment of one or more conditions of the patient, and
a notification module coupled to the control module and configured to alert the patient, wherein the control module is configured to initiate an alert using the notification module based on the assessment of one or more conditions of the patient.

8. An implantable medical device for use in assessment of one or more conditions of a patient comprising:
sensing apparatus to monitor physiological parameters of the patient, wherein the physiological parameters comprise the patient's posture and ejection time, wherein the patient's ejection time comprises at least one of the patient's left ventricular ejection time and right ventricular ejection time;
a sensing module coupled to the sensing apparatus and configured to receive the monitored physiological parameters; and
a control module coupled to the sensing module and configured to:
detect changes in the patient's posture between a lying position and an upright position using the monitored physiological parameters,
determine a plurality of posture-induced changes to the patient's ejection time over time using the monitored physiological parameters, wherein each of the plurality of posture-induced changes to the patient's ejection time comprise a difference between the patient's ejection time before a detected change in the patient's posture and the patient's ejection time after the detected change in the patient's posture,
store each of the plurality posture-induced changes to the patient's ejection time, and
analyze the plurality of posture-induced changes to the patient's ejection time over time to provide one or more trends to be used in an assessment of one or more conditions of the patient, wherein the one or more conditions of the patient comprises fluid overload.

9. The device of claim 8, wherein each of the plurality of posture-induced changes to the patient's ejection time comprise a difference between the patient's average ejection time over a first plurality of heart beats before the detected change in the patient's posture and the patient's average ejection time over a second plurality of heart beats after the detected change in the patient's posture.

10. The device of claim 8, wherein the control module is configured to analyze the one or more trends in the plurality of posture-induced changes to the patient's ejection time over time by determining whether the posture-induced changes to the patient's ejection time have been decreasing over time, wherein the control module is further configure to provide an assessment that indicates that the patient's heart is progressing towards heart failure if the posture-induced changes to the patient's ejection time have been decreasing over time.

11. The device of claim 8, wherein the physiological parameters further comprise the patient's heart rate, wherein the control module is further configured to:
determine a posture-induced change to the patient's heart rate using the monitored physiological parameters, wherein the posture-induced change to the patient's heart rate comprises a difference between the patient's heart rate before the detected change in the patient's posture and the patient's heart rate after the detected change in the patient's posture, store the posture-induced change to the patient's heart rate, and analyze the posture-induced change to the patient's heart rate to verify the assessment of one or more conditions of the patient.

12. A method for use in assessing one or more conditions of a patient comprising:

monitoring physiological parameters of the patient, wherein the physiological parameters comprise the patient's posture and ejection time, wherein the patient's ejection time comprises at least one of the patient's left ventricular ejection time and right ventricular ejection time;

detecting a change in the patient's posture between a lying position and an upright position using the monitored physiological parameters;

determining a posture-induced change to the patient's ejection time using the monitored physiological parameters, wherein the posture-induced change to the patient's ejection time comprises a difference between the patient's ejection time before the detected change in the patient's posture and the patient's ejection time after the detected change in the patient's posture;

storing the posture-induced change to the patient's ejection time; and analyzing the posture-induced change to the patient's ejection time to provide an assessment of one or more conditions of the patient, wherein the one or more conditions of the patient comprise fluid overload.

13. The method of claim 12, wherein the posture-induced change to the patient's ejection time further comprises a difference between the patient's average ejection time over a first plurality of heart beats before the detected change in the patient's posture and the patient's average ejection time over a second plurality of heart beats after the detected change in the patient's posture.

14. The method of claim 12, wherein the posture-induced change to the patient's ejection time further comprises a difference between the patient's average ejection time over a first predetermined period of time before the detected change in the patient's posture and the patient's average ejection time over a second predetermined period of time after the detected change in the patient's posture.

15. The method of claim 12, wherein analyzing the posture-induced change to the patient's ejection time comprises comparing the posture-induced change to the patient's ejection time to a baseline value.

16. The method of claim 12, wherein analyzing the posture-induced change to the patient's ejection time comprises comparing the posture-induced change to the patient's ejection time to a plurality of previous posture-induced changes to the patient's ejection time prior to the posture-induced change to the patient's ejection time to provide one or more trends to be used in the assessment of one or more conditions of the patient.

17. The method of claim 12 further comprising at least one of:

initiating or adjusting cardiac therapy to the patient based on the assessment of one or more conditions of the patient; and alerting the patient based on the assessment of one or more conditions of the patient.

18. A method for use in assessment of one or more conditions of a patient comprising:

monitoring physiological parameters of the patient, wherein the physiological parameters comprise the patient's posture and ejection time, wherein the patient's ejection time comprises at least one of the patient's left ventricular ejection time and right ventricular ejection time;

detecting changes in the patient's posture between a lying position and an upright position using the monitored physiological parameters, determining a plurality of posture-induced changes to the patient's ejection time over time using the monitored physiological parameters, wherein each of the plurality of posture-induced changes to the patient's ejection time comprise a difference between the patient's ejection time before a detected change in the patient's posture and the patient's ejection time after the detected change in the patient's posture, storing each of the plurality posture-induced changes to the patient's ejection time, and analyzing one or more trends in the plurality of posture-induced changes to the patient's ejection time over time to provide an assessment of one or more conditions of the patient, wherein the one or more conditions of the patient comprises fluid overload.

19. The method of claim 18, wherein each of the plurality of posture-induced changes to the patient's ejection time comprise a difference between the patient's average ejection time over a first plurality of heart beats before the detected change in the patient's posture and the patient's average ejection time over a second plurality of heart beats after the detected change in the patient's posture.

20. The method of claim 18, wherein analyzing the one or more trends in the plurality of posture-induced changes to the patient's ejection time over time comprises:

determining whether the posture-induced changes to the patient's ejection time have been decreasing over time, and providing an assessment that indicates that the patient's heart is progressing towards heart failure if the posture-induced changes to the patient's ejection time have been decreasing over time.

21. The method of claim 18 further comprising:

determining a posture-induced change to the patient's heart rate time using the monitored physiological parameters, wherein the posture-induced change to the patient's heart rate comprises a difference between the patient's heart rate before the detected change in the patient's posture and the patient's heart rate after the detected change in the patient's posture, storing the posture-induced change to the patient's heart rate, and analyzing the posture-induced change to the patient's heart rate to verify the assessment of one or more conditions of the patient.

22. The method of claim 18, wherein analyzing one or more trends in the plurality of posture-induced changes to the patient's ejection time over time comprises analyzing one or more trends in the plurality of posture-induced changes to the patient's ejection time that occur at the same time of the day.

* * * * *